United States Patent
Ogawa et al.

(10) Patent No.: US 7,781,600 B2
(45) Date of Patent: Aug. 24, 2010

(54) PROCESS FOR PURIFYING HYDROXYCARBOXYLIC ACID, PROCESS FOR PRODUCING CYCLIC ESTER, AND PROCESS FOR PRODUCING POLYHYDROXYCARBOXYLIC ACID

(75) Inventors: Tomoyuki Ogawa, Fukushima-Ken (JP); Tomohiro Hoshi, Fukushima-Ken (JP); Tsutomu Kushida, Fukushima-Ken (JP); Kentaro Otawara, Fukushima-Ken (JP)

(73) Assignee: Kureha Corporation, Tokyo (JP)

( * ) Notice: Subject to any disclaimer, the term of this patent is extended or adjusted under 35 U.S.C. 154(b) by 399 days.

(21) Appl. No.: 11/792,234

(22) PCT Filed: Oct. 17, 2005

(86) PCT No.: PCT/JP2005/019434

§ 371 (c)(1),
(2), (4) Date: Jun. 4, 2007

(87) PCT Pub. No.: WO2006/064611

PCT Pub. Date: Jun. 22, 2006

(65) Prior Publication Data

US 2008/0214842 A1  Sep. 4, 2008

(30) Foreign Application Priority Data

Dec. 17, 2004  (JP) .............................. 2004-365808

(51) Int. Cl.
  *C07C 51/42* (2006.01)
  *C07C 59/00* (2006.01)
  *C07D 319/00* (2006.01)

(52) U.S. Cl. .......... 549/274; 562/579; 562/580
(58) Field of Classification Search ................ 528/361; 562/579, 580; 549/274
See application file for complete search history.

(56) References Cited

U.S. PATENT DOCUMENTS

| 5,412,067 A | 5/1995 | Shinoda et al. |
| 2005/0020853 A1 | 1/2005 | Kuroda et al. |

FOREIGN PATENT DOCUMENTS

| DE | 28 10 975 A1 | 9/1979 |
| EP | 0 588 222 A2 | 3/1994 |

(Continued)

OTHER PUBLICATIONS

Supplementary European Search Report issued Feb. 15, 2010 in corresponding European Patent Application No. 05795776.3.

*Primary Examiner*—Taylor Victor Oh
(74) *Attorney, Agent, or Firm*—Wenderoth, Lind & Ponack, L.L.P.

(57) ABSTRACT

Disclosed is a process for purifying a hydroxycarboxylic acid, comprising: a crystallization step of subjecting a hydroxycarboxylic acid aqueous solution to crystallization for purification, a separation step of separating a hydroxycarboxylic acid crystal from a mother liquid, and a washing step of washing the hydroxycarboxylic acid crystal for further purification with a washing liquid, wherein the washing liquid is a hydroxycarboxylic acid aqueous solution. The purified or refined hydroxycarboxylic acid obtained through the above process is suitably used as a starting material for production of a polyhydroxycarboxylic acid. The above process is suitably included in a process for producing a cyclic ester and a process for producing a polyhydroxycarboxylic acid.

13 Claims, 1 Drawing Sheet

FOREIGN PATENT DOCUMENTS

| | | | | | |
|---|---|---|---|---|---|
| EP | 0 624 613 A2 | 11/1994 | JP | 7-155643 | 6/1995 |
| EP | 1 471 048 | 10/2004 | JP | 2001-321697 | 11/2001 |
| | | | JP | 2003-093924 | 4/2003 |
| | | | WO | 03/064366 | 8/2003 |

PROCESS FOR PURIFYING HYDROXYCARBOXYLIC ACID, PROCESS FOR PRODUCING CYCLIC ESTER, AND PROCESS FOR PRODUCING POLYHYDROXYCARBOXYLIC ACID

TECHNICAL FIELD

The present invention relates to a process for purifying or refining a hydroxycarboxylic acid suitable as a starting material for production of a polyhydroxycarboxylic acid, a process for producing a cyclic ester including the purification or refining process and a process for producing a polyhydroxycarboxylic acid.

BACKGROUND ART

Polyhydroxycarboxylic acids (aliphatic polyesters), such as polyglycolic acid and polylactic acid, can be degraded or decomposed by microorganisms or enzymes present in natural environments including soils and sea waters and are accordingly noted as biodegradable polymer materials exerting little load to the environments. Further, as polyhydroxycarboxylic acids are degradable and absorbable in vivo, they are also used as polymeric materials for medical use, such as surgical sutures and artificial skins.

Among the polyhydroxycarboxylic acids, polyglycolic acid is excellent in gas-barrier properties inclusive of oxygen gas-barrier property, carbon dioxide gas-barrier property and water vapor barrier property and also excellent in heat resistance and mechanical strength, so that the development for various use thereof as a single material or in a composite form together with another resin material is undertaken in the fields of packaging materials, etc.

A polyhydroxycarboxylic acid can be synthesized by dehydropolycondensation of a hydroxycarboxylic acid, such as glycolic acid (hydroxyacetic acid) or lactic acid (hydroxypropanoic acid), whereas in order to effectively produce a high-molecular weight aliphatic polyester, there has been generally adopted a process of synthesizing a bimolecular cyclic ester of the hydroxycarboxylic acid and subjecting the cyclic ester to ring-opening polymerization. For example, the ring-opening polymerization of glycolide (i.e., bimolecular cyclic ester of glycolic acid) provides polyglycolic acid, and the ring-opening polymerization of lactide (i.e., bimolecular cyclic ester of lactic acid) provides polylactic acid.

In any case, as a starting material for a polyhydroxycarboxylic acid with a high molecular weight and little abnormal linkage content, a hydroxycarboxylic acid is required to have a high purity to some extent, but an industrially available hydroxycarboxylic acid is inevitably accompanied with impurities actually. For example, glycolic acid obtained by carbonylation of formaldehyde in water, in the presence of an organic acid and sulfuric acid as catalysts, contains glycolic acid dimer or oligomer formed by ester-forming dehydrocondensation of glycolic acid and di-glycolic acid $(OCCH_2COOH)_2$ that is a dimer formed by ether-forming dehydrocondensation of glycolic acid as major impurities in addition to residues of the catalysts. Then, minor components such as the catalyst residues and ionic impurities can be easily separated and removed industrially by such means as adsorption or ion exchange, but a separate means is required for removal of organic impurities. For example, a patent document, WO92/05138 describes that a 70% technical-grade glycolic acid aqueous typically shows the following composition:

| | |
|---|---|
| glycolic acid | 62.4 wt. % |
| glycolic acid dimer | 8.8 wt. % |
| di-glycolic acid | 2.2 wt. % |
| methoxyacetic acid | 2.2 wt. % |
| formic acid | 0.24 wt. %. |

As general methods for purification or refining by separation of organic materials, unit operations, such as distillation and crystallization, are known. The application of such a purification or refining method to purification of a hydroxycarboxylic acid is, however, accompanied with an inherent difficulty that a hydroxycarboxylic acid readily causes polycondensation under heating. In view of this, distillation involving heating as an essential factor is basically difficult to be adopted. On the other hand, the crystallization from a hydroxycarboxylic acid aqueous solution is essentially a method of applying little thermal load to the hydroxycarboxylic acid but is still accompanied with a difficulty that polycondensation of the hydroxycarboxylic acid is liable to occur when the concentration adopted for efficient crystallization is excessively performed. For this reason, it has been proposed to effect the crystallization from an aqueous for production of a high-purity glycolic acid including the addition of seed crystal (WO 92/05138, mentioned above), whereas the recovery yield of glycolic acid by the crystallization is as extremely low as 6.6%-24% as the process does not include a step of concentrating the aqueous solution while obviating the difficulty of such a concentration step. Such a low yield may be tolerable for production of glycolic acid as a starting material for fine chemical synthesis but is not practical for production of a hydroxycarboxylic acid (glycolic acid) as a starting material for production of polyhydroxycarboxylic acids to be supplied as general-purpose resin products. On the other hand, another patent document, WO 02/22545 discloses an example wherein 327 g of 91 wt. %—lactic acid aqueous solution was subjected to crystallization and centrifugation to obtain 150 g of lactic acid crystal at a yield of 54%, but the technique is a laboratory-scale one and cannot be an industrially feasible process for producing a hydroxycarboxylic acid.

DISCLOSURE OF INVENTION

Accordingly, a principal object of the present invention is to provide an industrially feasible process for purifying a hydroxycarboxylic acid as a starting material for production of a polyhydroxycarboxylic acid, a process for producing a cyclic ester including the purification process and a process for producing a polyhydroxycarboxylic acid.

As a result of our study with the above object and repetition of various experiments, we have had a knowledge that it is possible to purify or refine (or produce) a hydroxycarboxylic acid at an industrially feasible high yield by crystallization (or partial crystallization) that exerts little thermal load to the hydroxycarboxylic acid at a level of purity that is sufficient as a starting material for production of a polyhydroxycarboxylic acid. Based on the knowledge, the process for purifying a hydroxycarboxylic acid according to the present invention, comprises: a process for purifying a hydroxycarboxylic acid comprising a crystallization step of subjecting a hydroxycarboxylic acid aqueous solution to crystallization for purification, a separation step of separating a hydroxycarboxylic acid crystal from a mother liquid, and a washing step of washing the hydroxycarboxylic acid crystal for further purification with a washing liquid, wherein the washing liquid is a hydroxycarboxylic acid aqueous solution.

Further, the process for producing a cyclic ester according to the present invention, comprises: subjecting a hydroxycarboxylic acid purified through the above-mentioned process, as it is or after dissolution in water, to polycondensation to form an oligomer of the hydroxycarboxylic acid, and de-polymerizing the oligomer to form a cyclic ester that is a dimer of the hydroxycarboxylic acid. This is based on a knowledge that the above-mentioned process for purifying a hydroxycarboxylic acid according to the present invention is effective for reducing an ether-form hydroxycarboxylic acid dimer (e.g., diglycolic acid) functioning as an impurity obstructing the de-polymerization of the oligomer.

Further, the process for producing a polyhydroxycarboxylic acid according to the present invention comprises: subjecting the cyclic ester produced through the above process to ring-opening polymerization.

BEST MODE FOR PRACTICING THE INVENTION

Figure 1:
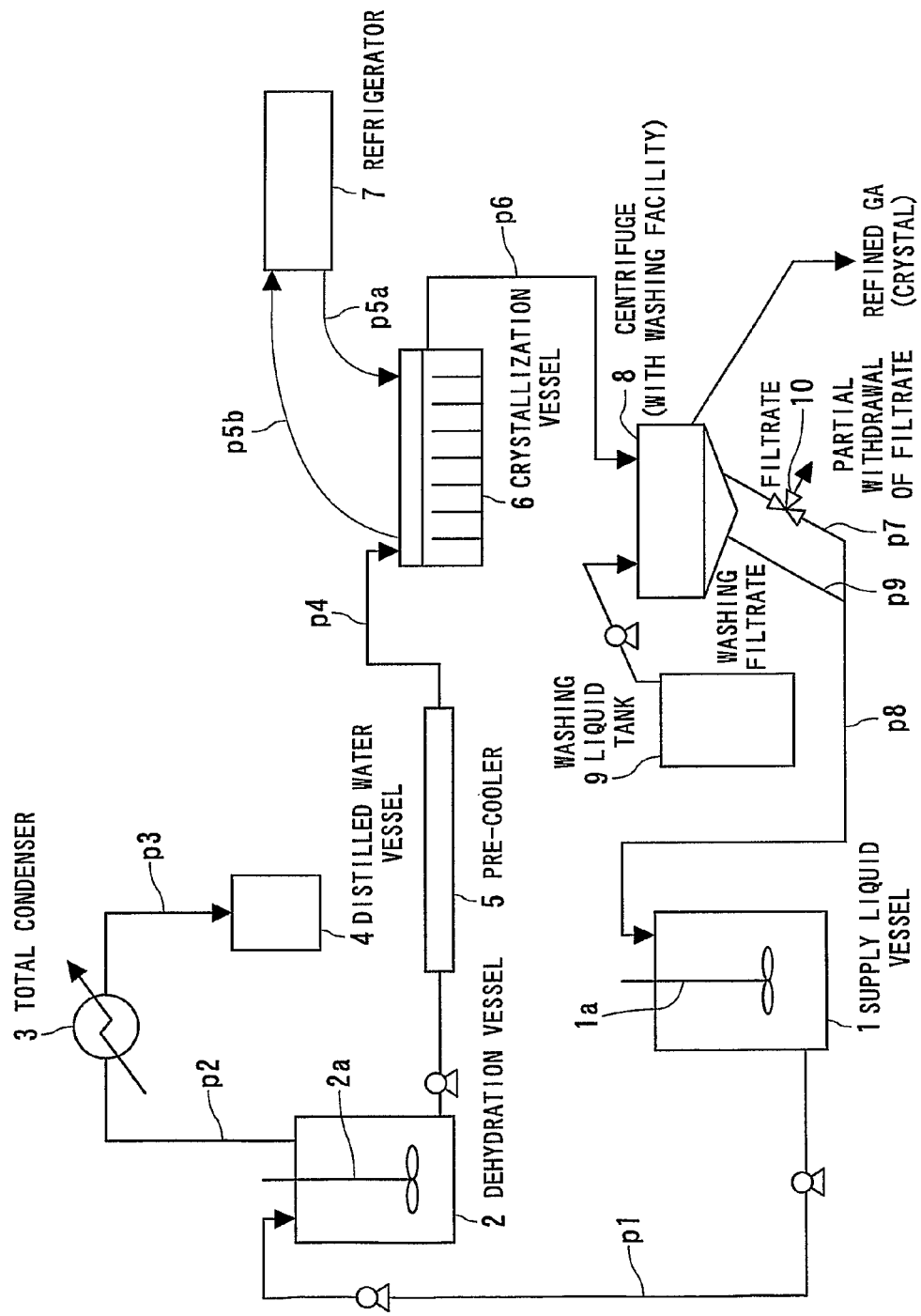
FIG. 1 is a schematic layout of an apparatus system suitable for practicing a process for purifying a hydroxycarboxylic acid according to the present invention.

The hydroxycarboxylic acid processed according to the present invention is preferably an α-hydroxycarboxylic acid which is solid at room temperature, such as glycolic acid, lactic acid, α-hydroxyvaleric acid, or α-hydroxybutyric acid. The production process is not particularly restricted, inclusive of fermentation process, synthesis process, etc. This is because an industrially supplied hydroxycarboxylic acid (aqueous solution) is inevitably accompanied with commingling of impurities regardless of any process through which it is produced. Among the hydroxycarboxylic acids, glycolic acid is suitable to be processed by the purification process of the present invention since it has a strong inclination of poly-condensation under heating.

Hereinbelow, the present invention is described in further detail with primary reference to application to glycolic acid, that is a preferred embodiment of the present invention. In the following description, "%" representing a quantity ratio means "wt. %" unless otherwise noted specifically.

(Process for Purifying a Hydroxycarboxylic Acid)

FIG. 1 is a schematic layout of an apparatus system suitable for practicing a process for purifying a hydroxycarboxylic acid according to the present invention. Here is explained an embodiment of continuously processing, as a starting liquid, a 70% technical-grade aqueous solution of glycolic acid (hereinafter sometimes referred to as "GA") containing 1% concentration of di-glycolic acid (sometimes referred to as "di-GA") as a typical impurity. The reason for selecting "di-GA" as a representative impurity is that a smaller amount of impurity is preferentially removed as a characteristic of crystallization and glycolic acid dimer as another impurity is less harmful in production of polyglycolic acid.

Referring to FIG. 1, a supply liquid vessel 1 equipped with a stirrer 1a reserves a glycolic acid aqueous solution having concentrations of, typically 70% of GA and 9.3% of di-GA (having a larger concentration than in the starting liquid as a result of continuous processing of the starting liquid). Generally, the GA concentration in the glycolic acid aqueous solution is preferably at most ca. 80%, more preferably ca. 65-75%.

The glycolic acid aqueous solution in the supply liquid vessel 1 is supplied via a pipe p1 to a dehydration vessel 2 equipped with a stirrer 2a and heating means (not shown). The dehydration vessel 2 is used for removing water forming a portion, e.g., 30% or less, of the supplied glycolic acid aqueous solution in order to increase the GA concentration in the glycolic acid aqueous solution up to a concentration efficient for a subsequent crystallization treatment. Generally, the glycolic acid aqueous solution is heated therein to, e.g., ca. 110-130° C. under a normal pressure or a reduced pressure, and the evaporated water is guided through a pipe p2 at the top of the dehydration vessel 2 to a total condenser 3 to be totally condensed thereat. The condensed water is sent via a pipe p3, held in a distilled water vessel 4 and thereafter discharged out of the system. In the dehydration vessel 2, GA concentration is adjusted to 50-90%, preferably 60-85%, more preferably ca. 70-80% (e.g., ca. 80%). If GA concentration is below 50%, the efficiency of the subsequent crystallization step is lowered, and in excess of 90%, the slurry viscosity is increased due to condensation of GA, thus rendering solid-liquid separation difficult, so that it becomes difficult to increase the purification efficiency according to the purification process of the present invention. For a similar reason, a water removal ratio in excess of 30% in the dehydration vessel 2 is not preferred. A small amount (ca. 1%) of GA that is possibly contained in the distilled water can be substantially wholly recovered to provide an increased yield if a partial condenser is placed before the total condenser 3, preferably in a portion ascending from the dehydration vessel 2 of the pipeline p2.

Then, the glycolic acid aqueous solution with an adjusted GA concentration is optionally cooled to ca. 50-20° C. by a pre-cooler 5 disposed as desired at a pipeline p4 and introduced to a crystallization vessel 6 where the glycolic acid aqueous solution is cooled down to a temperature (crystallization temperature) in a range of −20° C. (a eutectic point of GA and water) to ca. 5° C., and a portion of GA exceeding a saturation concentration at the crystallization temperature is caused to crystallize. The crystallization vessel (or crystallizer) 6 may be one having an organization allowing production of relatively large crystals due to countercurrent heat conduction with a coolant (e.g., ethylene glycol aqueous solution) circulatively supplied from a refrigerator 7 via pipes p5a and p5b. A commercially available example thereof is a horizontal multi-stage cooling crystallizer "CDC (Cooling Disc Crystallizer)" available from Gauda N.V., Netherlands.

The GA aqueous solution containing crystallized GA from the crystallization vessel 6 is then sent via a pipe p6 to a separator or centrifuge 8 having a washing facility (a commercially available example of which is a De-Corne-type continuous centrifuge available from Tanabe Wilcock K.K.) to be separated into GA crystal and a washing filtrate liquid. The filtrate liquid is circulated via a pipe p7 from the bottom of the separator 8 and a circulating pipe p8 to the supply liquid vessel 1. On the other hand, GA crystal is washed with a washing liquid supplied continuously or intermittently from a washing liquid tank 9 to the separator 8 and then recovered as refined GA (crystal). The washing filtrate liquid is circulated via a pipe p9 from the bottom of the separator 8 and the circulating pipe p8 to the supply liquid vessel 1.

The separator 8 may preferably be a separator having a washing facility (i.e., a separator having means for washing a crystal precipitated and once-separated from the liquid with an additional washing liquid and additional solid-liquid separation for recovery of the washed crystal), particularly a centrifuge having a washing facility as described above. This type of separator is preferred in order to effectively obviate the difficulties of an ordinary process of re-slurrying once-precipitated and separated crystal by mixing with a washing liquid and subjecting the re-slurry again to solid-liquid separation, such that (a) the mother liquid attached to the separated crystal and the washing liquid are completely mixed with each other and then subjected to additional solid-liquid separation, so that impurities are liable to remain in the crystal, and (b) the crystal is dissolved within the washing liquid during the re-slurrying so that the yield of the crystal is lowered. More specifically, in a centrifuge provided with a washing facility, the crystal separated from the mother liquid is placed under the action of a centrifugal force, and a washing liquid is allowed to be poured onto and from the inside of the crystal in that state, so that the mother liquid attached to the crystal is pushed and washed away with the washing liquid to enhance the washing effect. Further, only a short time is required for the contact between the washing liquid and the crystal, so that the lowering of yield due to dissolution of the crystal can be suppressed.

Further, the reason for the use of a glycolic acid aqueous solution as the washing liquid is that it can prevent a lowering in recovery yield of refined GA crystal through the crystallization step due to the use of a washing liquid not containing GA that causes an excessive dissolution of the resultant GA crystal in the washing liquid. From the viewpoint of preventing the dissolution of GA crystal to increase the recovery yield, it is preferred to use a saturated GA aqueous solution, whereas it is generally suitable to use a starting glycolic acid aqueous solution to be processed by the process of the present invention having a somewhat lower GA concentration than the saturated solution (e.g., a 70% technical-grade glycolic acid aqueous solution as mentioned above), as it is or after concentration to form a saturated glycolic acid aqueous solution. As a result, the entire process for purifying glycolic acid can be rendered continuous. As the entire process is rendered continuous, the impurities of di-GA, etc., are accumulated in the system, so that a withdrawal valve 10 is provided at the pipe p7 from the bottom of the separator 8, and a portion of the filtrate liquid from the separator 8 is withdrawn at an appropriate time and discharged out of the system, thereby stabilizing the concentrations of the impurities in the system (i.e., in the supply liquid vessel 1) at constant (including, e.g., a di-GA concentration of ca. 9.3% as mentioned above). When the withdrawal and discharge rate of the filtrate liquid is increased, the impurity concentrations in the system are lowered to increase the purity of the refined GA crystal, while the recovery yield of the GA crystal is lowered. When the withdrawal and discharge rate of the filtrate liquid is lowered, the reverse results hold true. Thus, by increasing or decreasing the withdrawal and discharge rate of the filtrate liquid, it is possible to control the purity (i.e., the percentage removal of the impurities) and the recovery yield of the refined GA crystal. For example, it was possible to obtain refined GA having an impurity removed percentage of slightly less than 90% based on a di-GA concentration as a measure at a yield of 95% or higher (See Example 1 described later).

MODIFICATIONS

In the above, a preferred embodiment of applying the process for purifying a hydroxycarboxylic acid of the present invention to glycolic acid has been described, but it is believed readily understandable to one of ordinary skill in the art that the above-mentioned embodiment can be modified in various manners within the scope of the present invention.

For example, the pre-cooler 5 provided at the pipe 4 can be replaced with a heat exchanger so as to allow a heat exchange with a low-temperature filtrate liquid from the pipe p8, thereby preliminarily cooling the glycolic acid aqueous solution supplied to the crystallization vessel 6. Further, the centrifuge 8 can be replaced by a solid-liquid separator, such as a vibration sieve or a filtration drier (e.g., "WD FILTER", made by Nissen, K.K.), each having a washing facility.

Further, the apparatus system for purification of hydroxycarboxylic acid of the present invention described with reference to FIG. 1 is essentially also applicable to hydroxycarboxylic acids other than glycolic acid. For example, in the case of lactic acid having a lower thermal polycondensability than glycolic acid, some differences are involved such that the lactic acid concentration in the system can be increased, and a somewhat lower crystallization temperature is preferred because of a higher solubility in water than glycolic acid, whereas the other conditions are similarly applicable thereto.

(Process for Production of a Cyclic Ester)

In the process for producing a cyclic ester according to the present invention, a hydroxycarboxylic acid purified through the above-mentioned process is polycondensed as it is or after being formed into an aqueous solution thereof in view of easiness of handling thereof, optionally followed by concentration, to be polycondensed into an oligomer of the hydroxycarboxylic acid, and the oligomer is de-polymerized to form a cyclic ester that is a dimer of the hydroxycarboxylic acid.

For example, in the case where the hydroxycarboxylic acid is glycolic acid, the glycolic acid purified through the above-mentioned process can be used as it is, but in view of the easiness of handling thereof, it is possible to dissolve the glycolic acid in water to form a glycolic acid aqueous solution (of which the concentration is suitably 70% or below), concentrate and polycondense the glycolic acid aqueous solution to recover a glycolic acid oligomer, and further depolymerize the glycolic acid oligomer according to a process described in International Publication WO 02/14303 to obtain glycolide (i.e., a cyclic dimer ester of glycolic acid). More specifically, according to the process of the above mentioned International Publication WO 02/14303 (the entire disclosure thereof is incorporated herein by reference)

(I) a mixture of glycolic acid oligomer (A) recovered in the above-described manner with a polyalkylene glycol ether (B) represented by formula (1) below:

(wherein $R^1$ denotes a methylene group or a linear or branched alkylene group having 2-8 carbon atoms, $X^1$ denotes a hydrocarbon group, Y denotes an alkyl or aryl group having 2-20 carbon atoms, and p denotes an integer of at least 1 provided that in the case of p being 2 or larger, a plurality of $R^1$ can be identical to or different from each other) and also having a boiling point of 230-450° C. and a molecular weight of 150-450, is heated to a temperature (e.g., 230-320° C.) causing de-polymerization of the glycolic acid oligomer (A) under a normal pressure or a reduced pressure of 0.1-90 kPa;

(II) a solution state is formed wherein a melted phase of the glycolic acid oligomer (A) and a liquid phase comprising the polyalkylene glycol (B) form a substantially uniform phase;

(III) the solution state mixture is kept continually to distil off glycolide (cyclic ester) formed by the de-polymerization together with the polyalkylene glycol ether (B); and (IV) glycolide is recovered from the distilled product.

(Process for Production of a Polyhydroxycarboxylic Acid)

A cyclic ester obtained in the above-described manner is generally known to be a good starting material for producing a polyhydroxycarboxylic acid through ring-opening polymerization thereof.

For the ring-opening polymerization of a cyclic ester, it is preferred to adopt a process of melting the cyclic ester under heating in the presence of a catalyst, and then subjecting the cyclic ester in a molten state to ring-opening polymerization. The polymerization process is a bulk-state ring-opening polymerization process. The ring-opening polymerization of a cyclic ester in a molten state may be effected batch-wise or continuously by using a reaction vessel, or a tube-type, column-type or extruder-type reaction apparatus. It is generally preferred to adopt a method of bulk-state ring-opening polymerization in a polymerization vessel. For example, when glycolide is heated, the glycolide forms a molten liquid and is polymerized on continued heating to form a polymer. In case where the polymerization temperature is below a crystallization temperature of the solid polymer, the polymer is precipitated in the course of polymerization to finally obtain a solid polymer. The polymerization time can vary depending on the ring-opening polymerization process and polymerization temperature but may ordinarily be 10 min.-100 hours, preferably 30 min.-50 hours, further preferably 1-30 hours, in the case of ring-opening polymerization in a vessel. The polymerization conversion is generally at least 95%, preferably 98% or higher, further preferably 99% or higher. It is most preferred to effect a full conversion in order to minimize the remaining of unreacted monomer and increase the production efficiency.

Further, it is also preferred to adopt a process of transferring the cyclic ester in a molten state into a polymerization apparatus comprising a plurality of tubes (preferably having both ends that can be opened or closed) and proceeding with the ring-opening polymerization in an airtight state in each tube; or a process of proceeding the ring-opening polymerization of the cyclic ester in a molten state in a reaction vessel equipped with a stirrer, taking out a purified polymer, once cooling and solidifying the polymer and further continuing solid-state polymerization of the polymer at a temperature below the melting point of the polymer. These polymerization processes can be effected either batch-wise or in a continuous manner. In any process, by controlling the polymerization temperature in an airtight state (i.e., in a reaction system not including a gaseous phase), it is possible to produce a polymer having objective properties, such as molecular weight and melt-viscosity stably and at a good reproducibility.

In effecting the above-mentioned bulk-state ring-opening polymerization of cyclic ester, it is preferred to subject a cyclic ester containing water and/or alcohol as an initiator or/and a molecular weight-regulating agent with a total proton concentration in the cyclic ester as a controlling parameter. The details of such a process for producing a polyhydroxycarboxylic acid are disclosed in the description of PCT/JP2004/015557 and PCT/JP2004/016706, and the disclosure of these descriptions are incorporated herein by reference.

EXAMPLES

Hereinbelow, the process for purifying a hydroxycarboxylic acid according to the present invention will be described more specifically based on Examples (experimental examples).

Example 1

The process for purifying a hydroxycarboxylic acid according to the present invention, particularly the apparatus system therefor described with reference to FIG. 1, is suited for continuous operation, but for the purpose of performance evaluation on a laboratory scale, a simulation experiment of continuous operation was performed by taking a cycle starting from the supply of a glycolic acid aqueous solution from the supply liquid vessel 1 to the dehydration vessel 2 until the filtrate liquid recycle from the centrifuge 8 to the supply liquid vessel 1 (including unit operations of (1) dehydration, (2) crystallization, (3) solid-liquid separation and washing of crystal, and (4) recycle of the filtrate liquid) and repeating batchwise the unit operations in the cycle.

More specifically, in a first cycle, a glycolic acid aqueous solution having a GA concentration of 70% and an impurity di-GA concentration of 1% was supplied to the dehydration vessel 2 and subjected to 18 cycles for repetition of operations similar to operations (1)-(4) shown below (wherein the GA concentration, di-GA concentration, etc. were different in successive cycles since the experiment represented a transitional state), whereby the filtrate liquid recycled to the supply liquid vessel 1 reached a substantially constant state including a GA concentration of 70% and a di-GA concentration of 9.29%. Accordingly, the state was judged as a steady state in a continuous operation, and the following operations (1)-(4) in a subsequent 19-th cycle as a simulation experiment for performance evaluation in continuous operation.

(1) Dehydration

Thus, 700 g of the glycolic acid aqueous solution exhibiting a constant state including a GA concentration of 70% and a di-GA concentration of 9.29% was heated to 120° C. at a normal presence to be concentrated up to a GA concentration of 80%.

(2) Crystallization

The glycolic acid aqueous solution concentrated up to a GA concentration of 80% was cooled down to −10° C. at a cooling speed of 0.2° C./min. to obtain a slurry containing precipitated GA crystals.

(3) Solid-Liquid Separation and Washing of Crystal.

The slurry obtained by the above-described crystallization was treated by a centrifuge ("CENTRIFUGAL FILTER: TYPE SYK-3800-10A", made by San'yo Rikagaku Kikai Seisakusho K.K.). The resultant crystal was mixed with an identical weight of a 70%—glycolic acid aqueous solution (i.e., the starting glycolic acid aqueous solution having a di-GA concentration of 1% and a GA concentration of 70%) as a washing liquid, and the resultant mixture was again treated by the centrifuge to obtain refined GA.

(4) Recycle of the Filtrate Liquid.

The filtrate liquid formed as a result of the first centrifugation of the slurry and the filtrate liquid formed as a result of the washing (i.e., the second centrifugation) in the above step (3) were mixed with each other and recycled to the supply liquid vessel 1 as a starting material for a subsequent cycle (20th cycle).

The yield of the refined GA obtained in the above step (3) (the ratio of the refined GA amount obtained in this 19th cycle with respect to the GA amount in the 70% glycolic acid aqueous solution used as the washing liquid in the preceding 18th cycle) was 95.5%, and the refined GA concentration was 97.6%. Further, the di-GA concentration in the refined GA was 0.16%, which corresponded to a di-GA concentration of 0.12% (=0.16×0.7/0.976) when converted to a 70% GA concentration in the starting solution, thus showing an impurity-removal percentage of 88% (=((1.0−0.12)/1.0)×100).

Examples 2-5

The following experiments were conducted in order to evaluate the influence of the degree of concentration of the glycolic acid aqueous solution in the dehydration step prior to the crystallization step on the refining effect.

(1) Dehydration

A steady state-glycolic acid aqueous solution identical to the one used in Example 1 and having a GA concentration of 70% and a di-GA concentration of 9.29% was concentrated to different degrees by heating under a normal pressure to form 4 glycolic acid aqueous solutions having GA concentrations of 70% (Example 2, no concentration), 80% (Example 3), 84% (Example 4) and 89% (Example 5), respectively. Each glycolic acid aqueous solution was subjected to the operations (2) and (3).

(2) Crystallization

Cooled down to 0° C. at a cooling speed of 0.2° C./min.

(3) Solid-Liquid Separation and Washing of Crystal

A slurry obtained in the above step (2) was subjected to Solid-liquid separation and Washing of crystal in the same manners as in the above-described Example 1.

The resultant four species of refined GA crystals exhibited percentages of crystallization, impurity di-GA concentrations and liquid contents as shown in Table 1 below.

TABLE 1

| Example | GA concentration before crystallization (%) | Percentage crystallization (%) | di-GA concentration (%) | Liquid content (%) |
|---|---|---|---|---|
| 2 | 70 | 15.2 | 0.08 | 4.2 |
| 3 | 80 | 19.5 | 0.10 | 4.6 |
| 4 | 84 | 24.6 | 0.28 | 13.4 |
| 5 | 89 | 27.5 | 0.40 | 19.5 |

The effect of concentration has appeared as an increased percentage of crystallization, and the adverse effects thereof have appeared as an increase in impurity di-G concentration (a lowering in refining efficiency) and an increase in liquid content (a lowering in efficiency of centrifugation as a result of increased slurry viscosity due to poly-condensation of GA). The results in the above Table 1 show that the concentration up to a GA concentration of ca. 80% can provide an increase in percentage crystallization (an increase in crystallization efficiency) without substantially adverse effects.

INDUSTRIAL APPLICABILITY

As described above, according to the present invention, there are provided a process for purifying a hydroxycarboxylic acid (a process for producing a refined hydroxycarboxylic acid) suitable as a starting material for production of a polyhydroxycarboxylic acid, a process for producing a cyclic ester including the purification process and a process for producing a polyhydroxycarboxylic acid. Further, in addition to the use as a starting material for production of a polyhydroxycarboxylic acid, the hydroxycarboxylic acid, such as glycolic acid, purified or refined by the process of the invention can also be used as a starting material for other chemical synthesis products for which an identical or lower purity is sufficient and also as a starting material in a purification process for obtaining a higher purity of hydroxycarboxylic acid, e.g., a crystallization process as described in the above-mentioned patent document, WO92/05138, which is although accompanied with a lower one-path yield.

The invention claimed is:

1. A continuous process for purifying a hydroxycarboxylic acid, comprising:
    a crystallization step of subjecting a hydroxycarboxylic acid aqueous solution to crystallization for purification, a separation step of separating a hydroxycarboxylic acid crystal from a mother liquid, and a washing step of washing the hydroxycarboxylic acid crystal for further purification with a washing liquid,
    wherein the washing liquid is a starting hydroxycarboxylic acid aqueous solution, a portion of the mother liquid separated from the hydroxycarboxylic acid crystal is discharged out of a system, and the remainder of the mother liquid and waste liquid after washing the hydroxycarboxylic acid crystal are recycled as the hydroxycarboxylic acid aqueous solution to be subjected to the crystallization step, thereby recovering refined hydroxycarboxylic acid at a yield of 95% or higher.

2. The process according to claim 1, wherein the washing step is performed by using a solid-liquid separator having a washing facility.

3. The process according to claim 2, wherein the solid-liquid separator is a centrifuge.

4. The process according to claim 1, wherein the hydroxycarboxylic acid aqueous solution is cooled before the crystallization step.

5. The process according to claim 1, wherein the hydroxycarboxylic acid aqueous solution subjected to the crystallization step has a hydroxycarboxylic acid concentration of at most 80 wt. %.

6. The process according to claim 5, wherein the hydroxycarboxylic acid aqueous solution subjected to the crystallization step has a hydroxycarboxylic acid concentration of 65-75 wt. %.

7. The process according to claim 1, wherein the hydroxycarboxylic acid is glycolic acid.

8. The process according to claim 5, further including a step of concentrating the hydroxycarboxylic acid aqueous solution up to a hydroxycarboxylic acid concentration of at most 80 wt. %.

9. A process for producing a cyclic ester, comprising the steps of:
    subjecting a hydroxycarboxylic acid purified through the process according to claim 1 to polycondensation to form an oligomer of the hydroxycarboxylic acid, and de-polymerizing the oligomer to form a cyclic ester that is a dimer of the hydroxycarboxylic acid.

10. The process according to claim 9, wherein an aqueous solution of the purified hydroxycarboxylic acid is concentrated and then subjected to the polycondensation to form an oligomer of the hydroxycarboxylic acid.

11. The process according to claim 9, wherein the hydroxycarboxylic acid is glycolic acid, and the cyclic ester is glycolide.

12. A process for producing a polyhydroxycarboxylic acid, comprising:
    subjecting the cyclic ester produced through the process of claim 9 to ring-opening polymerization.

13. The process according to claim 12, wherein the cyclic ester is glycolide, and the polyhydroxycarboxylic acid is polyglycolic acid.

* * * * *